(12) United States Patent
Lin et al.

(10) Patent No.: US 11,471,395 B2
(45) Date of Patent: Oct. 18, 2022

(54) METHOD FOR PREVENTING AGING WITH BIOACTIVE COMPOUND

(71) Applicant: TCI CO., LTD., Taipei (TW)

(72) Inventors: Yung-Hsiang Lin, Taipei (TW); Yu-Ling Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/099,785

(22) Filed: Nov. 17, 2020

(65) Prior Publication Data

US 2022/0054388 A1    Feb. 24, 2022

(30) Foreign Application Priority Data

Aug. 21, 2020    (TW) ................. 109128690

(51) Int. Cl.
| | | |
|---|---|---|
| *A61K 38/00* | (2006.01) | |
| *A61K 8/65* | (2006.01) | |
| *A61Q 19/00* | (2006.01) | |
| *A61Q 19/08* | (2006.01) | |

(52) U.S. Cl.
CPC .............. *A61K 8/65* (2013.01); *A61Q 19/007* (2013.01); *A61Q 19/08* (2013.01)

(58) Field of Classification Search
CPC ......... A61K 8/65; A61Q 19/007; A61Q 19/08
See application file for complete search history.

(56) References Cited

FOREIGN PATENT DOCUMENTS

| CN | 107581618 A | * | 1/2018 |
|---|---|---|---|
| TW | 201827452 A | | 8/2018 |
| TW | 202003587 A | | 1/2020 |

OTHER PUBLICATIONS

Kim et al. Study of Preventing Methods for Skin Aging and Wrinkles. Korean J. Oriental Physiology & Pathology 24(4):533~542, 2010 (Year: 2010).*
Breijyeh et al. Comprehensive Review on Alzheimer's Disease: Causes and Treatment. Molecules 2020, 25, 5789 (Year: 2020).*
Fulop et al. Aging, frailty and age-related diseases. Biogerontology (2010) 11:547-563 (Year: 2010).*
Harman, D. The aging process. Proc. Nati Acad. Sci. USA vol. 78, No. 11, pp. 7124-7128, Nov. 1981 (Year: 1981).*
Nutrition Insights. Tropical freshwater fish collagen holds strong wrinkle reducing capabilities, Vietnamese study finds. Accessed Sep. 14, 2021 at https://www.nutritioninsight.com/news/tropical-freshwater-fish-collagen-holds-strong-wrinkle-reducing-capabilities-vietnamese-study-finds.html (Year: 2018).*
NCBI Blast search results accessed Sep. 15, 2021 and available online May 13, 2020 (Year: 2020).*
Furtherfood.com accessed on Sep. 15, 2021 at https://www.furtherfood.com/fish-collagen/#:~:text=Fish%20skin%2C%20which%20is%20rich,fins%2C%20and%20bones%20as%20well.(Year: 2020).*
Bestow Beauty—collagen boost. Accessed Feb. 8, 2022 at https://bestowbeauty.com/bestow-collagen-boost/ Apr. 30, 2020 (Year: 2020).*
English language translation of CN107581618A obtained by Espacenet accessed May 9, 2022 (Year: 2017).*
Examination report dated Jun. 9, 2021, listed in correspondent Taiwan patent application No. 109128690.

* cited by examiner

*Primary Examiner* — Aradhana Sasan
*Assistant Examiner* — Mercy H Sabila
(74) *Attorney, Agent, or Firm* — Chieh-Mei Wang

(57) ABSTRACT

A method for preventing aging of a subject in need thereof includes administering to the subject a composition including a bioactive compound. The bioactive compound is a peptide, and includes at least one amino acid sequence as set forth in SEQ ID NO: 1 to SEQ ID NO: 6. Each of the amino acid sequence is a peptide of fish skin. The composition has anti-aging and cellular health maintaining capabilities. In addition, the composition can also be used for increasing collagen content, improving skin collagen density, improving skin moisture, minimizing skin pores, reducing wrinkles or achieving a combination of these effects.

2 Claims, 6 Drawing Sheets

Specification includes a Sequence Listing.

METHOD FOR PREVENTING AGING WITH BIOACTIVE COMPOUND

CROSS-REFERENCE TO RELATED APPLICATION

This non-provisional application claims priority under 35 U.S.C. § 119(a) to Patent Application No. 109128690 filed in Taiwan, R.O.C. on Aug. 21, 2020, the entire contents of which are hereby incorporated by reference.

REFERENCE OF AN ELECTRONIC SEQUENCE LISTING

The contents of the electronic sequence listing (US-2279-P200379USI_ST25.txt; Size: 5.907 KB: and Date of Creation: Nov. 17, 2020) is herein incorporated by reference in its entirety.

BACKGROUND

Technical Field

The present invention relates a method for preventing aging of a subject in need thereof, and more particularly to a method for preventing aging of the subject by administering to the subject a composition including a bioactive compound.

Related Art

*Pangasius bocourti*, also referred to as Basa, is an internationally important edible fish. Basa has rich nutrition, a short culture period and a high yield, and is easy to process. However, the rich subcutaneous fat of Basa tends to affect the flavor of Basa meat. Therefore, as internationally circulated edible fish, Basa is sold generally without fish skin. Further, a great number of fish skin wastes are generated.

In recent years, in order to reduce waste of resources and avoid environment pollution, attentions have been paid to the reuse of biowastes. In addition, fish skin is rich in collagen, and is often used for manufacturing processed food, gelatin and the like through secondary processing.

Collagen is a very important protein in the human body, and widely exists in connective tissues. Collagen acts as a main ingredient of tissues such as human body ligaments and eye corneas. In addition, collagen is also a main composition of the extracellular matrix. Collagen can enable the skin to maintain elasticity. Along with loss of collagen, the skin would also generate wrinkles.

However, collagen cannot be directly absorbed by the human body.

SUMMARY

In view of the aforementioned problem, the present invention provides methods for preventing aging of a subject in need by administering to the subject a composition including a bioactive compound, and the bioactive compound is a peptide.

In some embodiments, a method for preventing aging of a subject in need thereof including administering to the subject a composition including a bioactive compound is provided. The bioactive compound is a peptide. In addition, the peptide includes at least one amino acid sequence as set forth in SEQ ID NO: 1 to SEQ ID NO: 6. Each of the amino acid sequence is a peptide of the fish skin.

Based on the above, the peptide as the bioactive compound according to any embodiment can be used for preparing an anti-aging composition. In addition, the peptide includes at least one amino acid sequence as set forth in SEQ ID NO: 1 to SEQ ID NO: 6. Each of the amino acid sequence is a peptide of the fish skin. In some embodiments, the peptide as the bioactive compound can be used for promoting expression of anti-aging genes and/or improving mitochondria activities. In some embodiments, the anti-aging composition can be used for promoting expression of (COL3A1, COL4A4, HAS2 and HAS3 genes. In addition, the anti-aging composition can be used for increasing collagen content, increasing collagen density, increasing skin moisture, minimizing skin pores, reducing wrinkles or achieving a combination of these effects.

DETAILED DESCRIPTION

Figure 1:
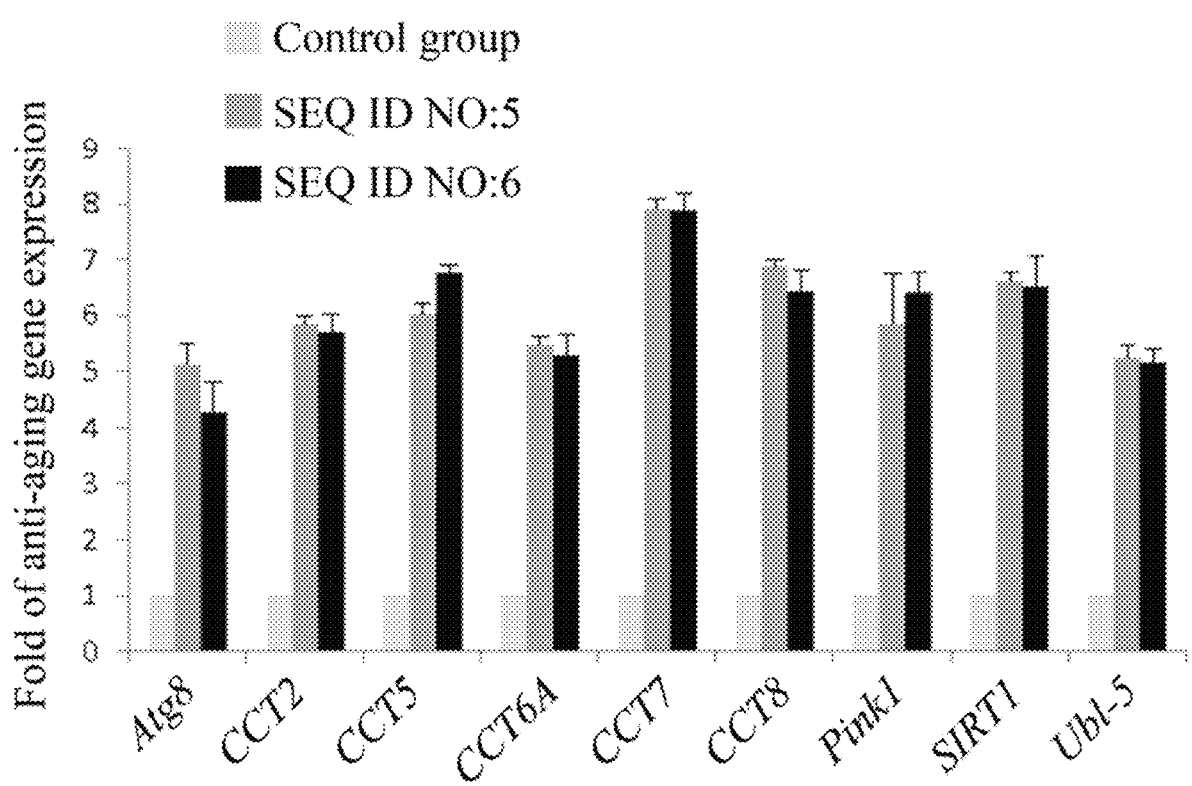
FIG. 1 is a bar chart showing folds of gene expression of anti-aging gene groups after treatment on human cells by a peptide in accordance with some embodiments of the present invention.

In some embodiments, a peptide used as a bioactive compound can be used for preparing an anti-aging composition. The peptide includes at least one amino acid sequence as set forth in SEQ ID NO: 1 to SEQ ID NO: 6. Each of the amino acid sequence is a peptide of fish skin.

It should be understood that the "peptide" contains a plurality of amino acids, the number of which is between that of an amino acid and that of a protein. In addition, the peptide as the bioactive compound may be an "isolated peptide" or a "synthesized peptide." The "isolated peptide" refers to a peptide isolated from an organism or an organism derivative, and this peptide has bioactivity. The "synthesized peptide" refers to a peptide synthesized by an instrument or an experimental operation according to an amino acid sequence of interest, and this peptide has bioactivity.

In some embodiments, the peptide as the bioactive compound can be obtained by isolation from the peptide of the fish skin or be synthesized by using an instrument or an experiment. For example, the source of the peptide of the fish skin includes fish skin cells, collagen (referred to as fish skin collagen hereafter) and fish muscle cells. Because a main ingredient in the fish skin is collagen, fish skin collagen mainly extracted in a process of extracting the fish skin collagen from the fish skin; however, proteins (i.e., fish skin cell proteins) in the fish skin cells and proteins (i.e., fish muscle cell proteins) of the fish muscle cells remaining on the fish skin may also be included. It should be understood that the term "peptide of the fish skin" described herein refers to a peptide including not only collagen as a main ingredient, but also peptides of the fish skin cell proteins and the fish muscle cell proteins.

In some embodiments, the fish skin is Basa skin. Therefore, the peptide as the bioactive compound is a peptide of Basa skin. The peptide of Basa skin can include a peptide of at least one of collagen, procollagen, fish skin cell proteins and fish muscle cell proteins, or a combination thereof. For example, collagen may be type IV collagen, type V procollagen, type XIV collagen and the like.

In addition, in some embodiments, the peptide as the bioactive compound may be a group of peptides resulted from mixing any of six amino acid sequences as set forth in SEQ ID NO: 1 to SEQ ID NO: 6 through chemical (such as enzymatic hydrolysis treatment) or/and physical (such as purification, isolation, hydrophilic and hydrophobic attraction and polar and non-polar solvents) treatment.

For example, a raw material from Basa skin can be isolated to obtain at least one amino acid sequence as set forth in SEQ ID NO: 1 to SEQ ID NO: 6. In addition, the raw material includes the peptide of fish skin collagen, the peptide of fish skin cell proteins and/or the peptide of fish muscle cell proteins. In an embodiment, the raw material may be commercially available Basa fish skin peptide powder (purchased from Italgelatin, Italy), or peptide powder formed by performing enzymatic hydrolysis treatment and drying on peptides extracted from Basa skin.

In some explanatory examples, the peptide as the bioactive compound can be isolated from Basa fish skin peptide powder by using an instrument (such as fast protein liquid chromatography and high-performance liquid chromatography system). In addition, in the above isolation process, at least one amino acid sequence as set forth in SEQ ID NO: 1 to SEQ ID NO: 6 may be isolated by using the properties (physical or chemical properties such as molecular weight, hydrophilic and hydrophobic properties and polar and non-polar properties) of the peptide.

In some embodiments, the molecular weight of each of the amino acid sequence is in a range of 700 Da to 1300 Da. In some embodiments, each of the amino acid sequence has 8 to 13 amino acids.

In some embodiments, when the peptide is capable of promoting expression of at least one anti-aging gene and includes at least one amino acid sequence as set forth in SEQ ID NO: 4 to SEQ ID NO: 5, the composition containing the peptide can be used for promoting the expression of at least one anti-aging gene. In addition, the composition can also be used for promoting the expression of at least one anti-aging gene, to improve the anti-aging function of the skin. For example, the at least one anti-aging gene includes at least one gene of Atg8 gene, CCT2 gene, CCT6A gene, CCT6A gene, CCT7 gene, CCT8 gene, Pink1 gene, STIR1 gene and Ubl-5 gene. Therefore, when any one or more of the amino acid sequences as set forth in SEQ ID NO: 4 to SEQ ID NO: 5 are selected to prepare the composition, the composition can be used for promoting the expression of at least one anti-aging gene.

In some embodiments, when the peptide includes at least one amino acid sequence as set forth in SEQ ID NO: 2 to SEQ ID NO: 6, the peptide can be used for improving mitochondria activities, and the composition containing the peptide can also be used for improving mitochondria activities, so as to maintain cellular health. For example, when any one or more of the amino acid sequences as set forth in SEQ ID NO: 2 to SEQ ID NO: 6 are selected to prepare the composition, the composition can be used for improving mitochondria activities.

In some embodiments, when the peptide includes at least one amino acid sequence as set forth in SEQ ID NO: 1 to SEQ ID NO: 6, the peptide can be used for preparing an anti-aging composition. The anti-aging composition can be used for increasing collagen density, increasing skin moisture, minimizing skin pores, reducing wrinkles or achieving a combination of these effects.

In some embodiments, the composition containing the peptide having at least one amino acid sequence as set forth in SEQ ID NO: 1 to SEQ ID NO: 6 can be used for improving skin conditions. For example, the composition containing the peptide having at least one amino acid sequence as set forth in SEQ ID NO: 1 to SEQ ID NO: 6 can have at least one of the following effects: increasing collagen content, increasing collagen density, increasing skin moisture, minimizing skin pores and reducing wrinkles.

For example, when the composition includes the peptide for promoting expression of at least one gene of a COL3A1 gene and a COL4A4 gene, the composition can be used for promoting generation of skin collagen, improving density of skin collagen, minimizing skin pores or achieving a combination of these effects. When the composition includes the peptide for promoting expression of at least one gene of an HAS2 gene and an HAS3 gene, the composition can be used for improving skin moisture. When the composition includes at least one gene of a COL3A1 gene, a COL4A4 gene, an HAS2 gene and an HAS3 gene, the composition can be used for reducing wrinkles.

In some embodiments, the composition containing the peptide having at least one amino acid sequence as set forth in SEQ ID NO: 1 to SEQ ID NO: 6 can be a food composition, a healthcare composition, or a pharmaceutical composition, etc. For example, the composition containing the peptide having at least one amino acid sequence as set forth in SEQ ID NO: 1 to SEQ ID NO: 6 can be edible peptide powder. Therefore, by taking the composition, the peptide included therein can regulate gene expression of skin cells for improving the conditions of the skin cells.

It should be understood that the term "regulating gene(s)" described herein may refer to "promoting the expression of gene(s)" or "inhibiting the expression of gene(s)."

Example I: Preparation of the Isolated Peptides

Firstly, 100 mg of Basa fish skin peptide powder (purchased from Italgelatin, Italy) was weighed and dissolved into 5 ml of a buffer solution A to obtain a peptide solution. The buffer solution A was prepared from a 50 mM Tris/HCl buffer solution (pH 8.0) and 100 mM sodium chloride (NaCl).

Then, a fast protein liquid chromatography instrument (FPLC purification instrument, from ÄKTA GE Healthcare Life Sciences, and referred to as a purification instrument hereafter) was used for coarse isolation of the peptide solution, so as to obtain a primary isolated peptide mixture. The separation column disposed in the purification instrument was a molecular sieve colloid purification column (sephadex G-25, 2.6 cm×10 cm, 53 ml). A flow rate of the purification instrument was set to 1 ml/min, and the ultraviolet light had wavelengths of 220 nm and 280 nm. The primary isolated peptide mixture having an absorption peak corresponding to 5 kDa or lower was subjected to lypholization at −80° C. (instrument brand: EYELA, model: FD-1000) for 12 h, so as to obtain a solid primary isolated peptide mixture.

30 mg of the solid primary isolated peptide mixture was dissolved into 2 ml of deionized water containing 0.1% trifluoroacetic acid (TFA), so as to obtain a pre-isolated peptide mixture. Then, the pre-isolated peptide mixture was separated by a high-performance liquid chromatography (HPLC) system (machine type: Hitachi Chromaster HPLC system; brand: Hitachi, Tokyo, Japan) (referred to as an HPLC system hereafter), so as to obtain a plurality of groups of isolated peptides. A molecular sieve C18 high-pressure column (model: TSKgel G2000SWXL; brand: Tosoh, 30 cm×7.8 mm, 5 μm) was disposed in the HPLC system. In set values of the HPLC system, a buffer solution A (i.e., a solution with 0.1% TFA dissolved into 100% deionized water) and a buffer solution B (i.e., a solution with 0.1% TFA dissolved into 100% ACN) were mixed according to a separation gradient. The separation gradient was 5% acetonitrile (ACN)/0.1% TFA to 100% ACN/0.1% TFA (i.e., the concentration gradient of the ACN was raised from 5% to 100% in a 0.1% TFA solution environment), the flow rate was set to 1 ml/min, and the column temperature was set to 40° C.

Therefore, the peptide in the primary isolated peptide mixture could be eluted out along with the HPLC solutions with different polarities and molecular weights, and the groups of isolated peptides were obtained. In addition, the groups of isolated peptides were subjected to lypholization at −80° C. (instrument brand: EYELA, model: FD-1000) for 12 h, so as to obtain a plurality of groups of solid isolated peptides.

Example II: Peptide Identification

The plurality of groups of isolated peptides in Example 1 were subjected to protein identification. Firstly, after reaching a concentration of 20 mg/mi by addition of deionized water, the groups of solid isolated peptides were subjected to protein identification by a liquid chromatography mass spectrometer (LC-MS/MS). The LC-MS/MS was a quadrupole-time-of-flight tandem mass spectrometer system (Q-TOF). The model of a liquid chromatography system (LC system) was UltiMate 3000 RSLCnano LC Systems (brand: Thermo Fisher Scientific), and the model of the mass spectrometer was TripleTOF® 6600 System (brand: Applied Biosystems Sciex).

The separation column disposed in the liquid chromatography system was a CIS separation column (Acclaim PepMap C18, 75 μm I.D.×25 cm nanoViper, 2 μm, 100 Å (Thermo Fisher Scientific)). A solution system used by the liquid chromatography mass spectrometer was a buffer solution A (i.e., a solution with 0.1% TFA dissolved into 100% deionized water) and a buffer solution B (i.e., a solution with 0.1% TFA dissolved into 100% ACN). A separation gradient set by the liquid chromatography mass spectrometer was 5% to 90% of the buffer solution B at the flow rate of 300 nl/min in 30 min.

In set values of the mass spectrometer, survey scan was set to scan all ionized isolated peptides in a range of 400 m/z (mass-to-charge ratio) to 1200 m/z. In an information dependent acquisition (CID) mode, a detection range of the peptide was set to 100-5000 Da. Then, these isolated peptides were analyzed, and a plurality of MS/MS spectra were correspondingly generated. These MS/MS maps were retrieved in databases (NCBI and UniProt) by a Mascot analysis program, so as to further obtain the amino acid sequences and identification information of these isolated peptides, as shown in Table 1 and Table 2.

TABLE 1

| Sequence number | Sequence | Molecular weight |
| --- | --- | --- |
| SEQ ID NO: 1 | KGWPGTPG | 798.40 |
| SEQ ID NO: 2 | PGAPGSSGPKG | 910.4509 |
| SEQ ID NO: 3 | VAEGAQGNIGPA | 1083.5196 |
| SEQ ID NO: 4 | NPGPHGQPGPPGP | 1224.5524 |
| SE0 ID NO: 5 | DKPLIPEGP | 964.5229 |
| SEQ ID NO: 6 | GPLGPIGPPGLP | 1070.6124 |

As shown in Table 1, in some embodiments, the molecular weight of the amino acid sequences of the isolated peptide was in a range of 700 Da to 1300 Da. In some embodiments, the isolated peptide has 8 to 13 amino acids.

TABLE 2

| Sequence number | Identification information |
| --- | --- |
| SEQ ID NO: 1 | Collagen, alpha-1 (IV) chain-like |
| SEQ ID NO: 2 | Collagen, type XIV |
| SEQ ID NO: 3 | Kinesin family member 21B |
| SEQ ID NO: 4 | Persistent plexus |
| SEQ ID NO: 5 | Titin, tandem duplicate 2 |
| SEQ ID NO: 6 | Procollagen, type V, alpha I |

In addition, as shown in Table 2, the amino acid sequence of the isolated peptide was a peptide of Basa skin. SEQ ID NO: 1 and SEQ ID NO: 2 were peptides of at least one type of collagen of Basa skin. SEQ ID NO: 6 was a peptide of a procollagen. SEQ ID NO: 3 was a peptide of a Kinesin family member 21B. SEQ ID NO: 4 was a peptide of a Persistent plexus. SEQ ID NO: 5 was a peptide of a Titin, tandem duplicate 2. Therefore, a raw material from Basa skin includes amino acid sequences of 6 types of isolated peptides as in SEQ ID NO: 1 to SEQ ID NO: 6.

Example III: Peptide Synthesis

In order to verify the effects of the amino acid sequences of the 6 types of isolated peptides on skin cells, synthesized peptides were prepared in the Example III according to the amino acid sequences identified in Example II (i.e., SEQ ID NO: 1 to SEQ ID NO: 6). The synthesis was a solid phase synthesis (Fmoc-Solid Phase Peptide Synthesis). In addition, the instrument was a peptide synthesis instrument (model: Focus XC III 0, America; brand: AAPPTEC).

The amino acid sequence of SEQ ID NO: 6 was taken as an example hereafter. The amino acid sequence of SEQ ID NO: 6 is Gly-Pro-Leu-Gly-Pro-Ile-Gly-Pro-Pro-Gly-Leu-Pro.

Step (1): Firstly, resin was put into a reaction tube and soaked in 15 ml of dichloromethane (DCM) per 1 g of resin for 30 min so that the resin expanded therein.

Step (2): The dichloromethane in the reaction tube was removed. According to a proportion of 15 ml of 20% piperidine dimethylformamide (piperidine DMF) per 1 g of resin, reaction was performed with the resin in piperidine DMF for 5 min. Then, solvent in the reaction tube was removed. Then, according to a proportion of 15 ml of 20% piperidine dimethylformamide solution per 1 g of resin, reaction was performed with the resin again for 15 min, so as to remove protecting groups on the resin and obtain deprotected resin.

Step (3): After the solution in the reaction tube was removed again, a few resin particles were taken out from the reaction tube for characterization. Firstly, the resin was washed for three times by ethanol, and one drip of ninhydrin solution and one drip of phenol solution were added. Heating was performed for 5 min at 105° C. to 110° C. When the ninhydrin solution and the phenol solution reacted with the resin and became dark blue, the reaction was positive, suggesting that the resin in the reaction tube was deprotected and could be combined with amino acids.

Step (4): According to a proportion of 10 ml of dimethylformamide per 1 g of resin, the deprotected resin was added to the reaction tube and repeatedly washed for 6 times.

Step (5): After three-time excessive protected glycine (Fmoc-Gly) and three-time excessive hydroxybenzotriazole (HOBt) were dissolved by a small amount of dimethylformamide, they were added into the reaction tube containing the deprotected resin to react for 90 min.

Step (6): After reacting for 90 min, according to a proportion of 10 ml of dimethylformamide per 1 g of resin, the resin attached with amino acids was repeatedly washed for 3 times.

Then, Step (2) to Step (6) were repeated until other amino acids (Pro, Leu, Gly, Pro, Iie, Gly, Pro, Pro, Gly, Leu and Pro) were sequentially attached to form a primary synthesized peptide with an amino acid sequence of SEQ ID NO: 6.

Step (7): According to a proportion of 10 ml of dimethylformamide per 1 g of resin, the primary synthesized peptide was repeatedly washed for 3 times. Then, according to a proportion of 10 ml of dichloromethane per 1 g of resin, the primary synthesized peptide was washed for 3 times. Finally, according to a proportion of 10 ml of ethanol per 1 g of resin, the primary synthesized peptide was washed for 3 times.

Step (8): The washed primary synthesized peptide was reacted with 10 g of lysis solution (86% of trifluoroacetic acid, 4% of thioanisole, 3% of water, 5% of ethanedithiol (EDT) and 2% of phenol) for 120 min, so as to separate the primary synthesized peptide from the resin.

Step (9): By a sandbag funnel, the lysis solution containing the primary synthesized peptide was separated from the resin. Then, the lysis solution containing the primary synthesized peptide was added to diethyl ether with a volume of eight times of the above lysis solution. Next, suction filtering separation was performed by a Buchner funnel so as to obtain primary synthesized peptide and the lysis solution. After evaporating the diethyl ether containing the lysis solution, the primary synthesized peptide was washed for three times by the diethyl ether. The primary synthesized peptide was solid. In addition, after the diethyl ether was volatilized at a room temperature, the dried primary synthesized peptide was obtained.

Step (10): After 1 mg of dried primary synthesized peptide was re-dissolved by 0.5 ml of deionized water, 20 ml of re-dissolved primary synthesized peptide was isolated and purified by an HPLC system (machine type: Hitachi Chromaster HPLC system; brand: Hitachi, Tokyo, Japan), so as to obtain a pure synthesized peptide. A C18 column (brand: Gemini-NX) was disposed in the HPLC system. A detection wavelength was set to 220 nm. In addition, in the HPLC system, a buffer solution A (i.e., a solution with 0.1% TFA dissolved into 100% deionized water) and a buffer solution B (i.e., a solution with 0.1% TFA dissolved into 100% V ACN) were mixed according to a linear separation gradient, to elute and separate out the synthesized peptide. A set value of the separation gradient was a linear gradient from 10% of the buffer solution B raised to 90% of ACN (dissolved into 0.1% TFA). The flow rate was set to 1 ml/min. The separation time was set to 30 min. In addition, a result that the purities of the synthesized peptides all reached 95% or above could be obtained by calculating the peak area of each of the synthesized peptide according to an HPLC chromatography. Therefore, the synthesized peptide including the amino acid sequence of SEQ ID NO: 6 could be obtained.

Likewise, other amino acid sequences (i.e., SEQ ID NO: 1 to SEQ ID NO: 5) were also be treated according to the above process. After Step (1), the above Step (2) to Step (6) were repeatedly performed until the amino acids were connected to form the corresponding amino acid sequences. Then, Step (7) to Step (10) were performed for washing and purification, so as to obtain purified (the purity being up to 95%) synthesized peptide (i.e., SEQ ID NO: 1 to SEQ ID NO: 5).

In order to confirm the effect of each of the amino acid sequences on gene expression in cells, human fibroblasts (CCD-966SK) and individual synthesized peptides were co-cultured, and then, gene expression in the cells was analyzed. 6 types of synthesized peptides were respectively subjected to cell experiments. In addition, the amino acid sequences of 6 types of synthesized peptides were respectively SEQ ID NO: 1, SEQ ID NO: 2, SEQ ID NO: 3, SEQ ID NO: 4, SEQ ID NO: 5 and SEQ ID NO: 6. The sequence numbers SEQ ID NO: 1 to SEQ ID NO: 6 will be referred to as groups.

(I) Experiment Materials and Experiment Groups

Cell gene expression test refers to that after the human fibroblasts (purchased from Food Industry Research and Development Institute) and samples to be tested (such as peptides or compositions) were co-cultured, then, RNA in the cells was collected for analysis. Referring to Table 3, the gene expression test groups were divided into 8 groups. 6 groups therein were peptide experiment groups (Experiment group A to Experiment group F), 1 group was a composition experiment group (Experiment group G), and 1 group was a control group. In addition, each of the group was co-cultured with $1 \times 10^5$ human fibroblasts in a cell culture plate containing 2 ml of cell culture medium (X-VIVO™ 10). Experiment group A to Experiment group F respectively corresponded to 6 groups of peptide experiment groups added with 6 types of synthesized peptides (SEQ ID NO: 1, SEQ ID NO: 2, SEQ ID NO: 3, SEQ ID NO: 4, SEQ ID NO: 5 and SEQ ID NO: 6) prepared according to Example III. Experiment group G was a composition experiment group added with the composition. In addition, the composition was identified in Example 11 to be Basa fish skin peptide powder (purchased from Italgelatin, Italy) containing 6 types of peptides (i.e., SEQ ID NO: 1, SEQ ID NO: 2, SEQ ID NO: 3, SEQ ID NO: 4, SEQ ID NO: 5 and SEQ ID NO: 6). No peptide or composition was added in Control group.

TABLE 3

| Gene expression test group | | Cell culture medium (2 ml) | Cells to be tested ($1 \times 10^5$) | Samples to be tested |
|---|---|---|---|---|
| SEQ ID NO: 1 peptide experiment group | Experiment group A | X-VIVO™ 10 | Human fibroblasts | 50 μg of SEQ ID NO: 1 peptide was added |
| SEQ ID NO: 2 peptide experiment group | Experiment group B | X-VIVO™ 10 | Human fibroblasts | 50 μg of SEQ ID NO: 2 peptide was added |
| SEQ ID NO: 3 peptide experiment group | Experiment group C | X-VIVO™ 10 | Human fibroblasts | 50 μg of SEQ ID NO: 3 peptide was added |
| SEQ ID NO: 4 peptide experiment group | Experiment group D | X-VIVO™ 10 | Human fibroblasts | 50 μg of SEQ ID NO: 4 peptide was added |
| SEQ ID NO: 5 peptide experiment group | Experiment group E | X-VIVO™ 10 | Human fibroblasts | 50 μg of SEQ ID NO: 5 peptide was added |
| SEQ ID NO: 6 peptide experiment group | Experiment group F | X-VIVO™ 10 | Human fibroblasts | 50 μg of SEQ ID NO: 6 peptide was added |
| Composition experiment group | Experiment group G | X-VIVO™ 10 | Human fibroblasts | 200 mg of composition was added |
| Control group | | X-VIVO™ 10 | Human fibroblasts | no peptide or composition was added |

(II) Experiment Design

For peptide experiment groups (corresponding to Experiment group A to Experiment group F), according to a proportion of 25 μg of synthesized peptide per 1 ml of cell culture medium, the human fibroblasts were cultured for 24 h at 37° C. For the composition experiment group (corresponding to Experiment group G), according to a proportion of 100 mg of composition per 1 ml of cell culture medium, the human fibroblasts were cultured for 24 h. For Control group, no peptide or composition was added, and the human fibroblasts were cultured for 24 h in a pure cell culture medium. Then, after culture for 24 h, the peptide-containing cell culture medium or the pure culture medium was removed from each of the group, and cells in each of the group were washed by a phosphate buffer solution (PBS) so as to remove the residual culture medium. The washed cells were spun down and were subjected to cell lysis by a cell lysis solution (purchased from Geneaid company, Taiwan, China). Then, RNA in each of the group of cells was extracted by an RNA extraction kit (purchased from Geneaid company, Taiwan, China). Next, the extracted RNA was subjected to inverse transcription to obtain cDNA by a cDNA synthesis reagent (purchased from Geneaid company, Taiwan, China). In addition, the intracellular gene expression was observed by a polymerase chain reaction (PCR) instrument using different primers (as shown in Table 4). In addition, the primers firstly reacted by a green fluorescent dye of SYBR green dye (Applied Biosystem), and quantification of gene expression was performed by a 2-ΔΔCt method. It should be noted that the gene expression in the drawings was shown in relative fold, ratio or percentage, where standard deviations were calculated by an STDEV formula of Excel software, and statistically significant differences were analyzed by one-tailed student t-test in the Excel software. In the drawings, "*" represents $p<0.05$, "" represents $p<0.01$, and "*" represents $p<0.001$. More "*" represents more significant statistical differences.

TABLE 4

| Primer | Sequence number | Sequence |
|---|---|---|
| COL3A1-F | SEQ ID NO: 7 | TGGTTGCACGGTAGGAAACAT |
| COL3A1-R | SEQ ID NO: 8 | ACAGCCTTGCGTGTTCGATA |
| COL4A4-F | SEQ ID NO: 9 | CTGGGTGCTGTGTGTTTTGA |
| COL4A4-R | SEQ ID NO: 10 | TGAGTCTTGTTTTGCCCTGC |
| HAS2-F | SEQ ID NO: 11 | CGGTGCTCCAAAAAGGCAAA |
| HAS2-R | SEQ ID NO: 12 | ACACAATGAGTTGGGCGAGA |
| HAS3-F | SEQ ID NO: 13 | CACCCATGGGGCTTAACTT |
| HAS3-R | SEQ ID NO: 14 | CTGCAGGTCCCAGTTCACAT |
| Atg8-F | SEQ ID NO: 15 | CCGCAGTAGGTGGCAAAGTA |
| Atg8-R | SEQ ID NO: 16 | GGAGTCGGAGAGGATTGCTG |
| CCT2-F | SEQ ID NO: 17 | CACTGGTGCGATTATTTG |
| CCT2-R | SEQ ID NO: 18 | CCCAGCAAATATCAGAAG |
| CCT5-F | SEQ ID NO: 19 | ATAAATGTGAGGCTGAATC |
| CCT5-R | SEQ ID NO: 20 | ACTFGTCACTTGTGGCAC |
| CCT6A-F | SEQ ID NO: 21 | TGTGTATCTTAATCCAGACTC |
| CCT6A-R | SEQ ID NO: 22 | CGTTTCACCTAAGAGTTGTC |
| CCT7-F | SEQ ID NO: 23 | GATTGGCCATTTAAGAAAC |

TABLE 4-continued

| Primer | Sequence number | Sequence |
|---|---|---|
| CCT7-R | SEQ ID NO: 24 | CCATACCCAAACCTAAGC |
| CCT8-F | SEQ ID NO: 25 | ACCCGGAGGTGGAGCAA |
| CCT8-R | SEQ ID NO: 26 | GGACATGTCTCTCCATATGATGTGA |
| Pink1-F | SEQ ID NO: 27 | GTGGAACATCTCGGCAGGTT |
| Pink1-R | SEQ ID NO: 28 | CCTCTCTTGGATTTTCTGTAAGTGAC |
| SIRT1-F | SEQ ID NO: 29 | TGCTGGCCTAATAGAGTGGCA |
| SIRT1-R | SEQ ID NO: 30 | CTCAGCGCCATGGAAAATGT |
| Ubl-5-F | SEQ ID NO: 31 | CCTCTTCCTCGTTCTACCGC |
| Ubl-5-R | SEQ ID NO: 32 | CTAGCTGGAGCTCGAATCGC |

(III) Expression Analysis of Anti-Aging Gene in Peptide Experiment Groups

Firstly, 6 groups of peptide experiment groups (i.e., Experiment group A to Experiment group F) and a control group were subjected to anti-aging gene test, as shown in FIG. 1 and Table 4. In addition, the anti-aging related genes of the skin include Atg8 gene (Gene ID: 11345), CCT2 gene (Gene ID: 10576), CCT5 gene (Gene ID: 22948), CCT6A gene (Gene ID: 908), CCT7 gene (Gene ID: 10574), CCT8 gene (Gene ID: 10694), Pink1 gene (Gene ID: 65018), SIRT1 gene (Gene ID: 23411) and UW-5 gene (Gene ID: 59286).

It should be understood that as listed in Table 3, a group marked as SEQ ID NO: 1 in the drawings equals to Experiment group A marked hereafter, and so on. Groups marked as SEQ ID NO: 1, SEQ ID NO: 2, SEQ ID NO: 3, SEQ ID NO: 4, SEQ ID NO: 5 to SEQ ID NO: 6 in the drawings respectively and correspondingly equal to Experiment group A to Experiment group F marked hereafter.

Studies showed that when the mRNA corresponding to the CCT2 gene, CCT5 gene, CCT6A gene, CCT7 gene and CCT8 gene in nematodes was increased, nematode cells could be recovered into undifferentiated stem cells to further prolong the lifetime of the nematodes. Therefore, when the expression levels of the CCT2 gene, CCT5 gene, CCT6A gene, CCT7 gene and CCT8 gene were increased, the anti-aging capability of the cells was increased. In addition, studies also showed that when mutated DNA was accumulated in the cells, cell aging could be accelerated; and when the expression levels of the Atg8 gene and Pink1 gene were increased, the mutated DNA could be cleared out. Therefore, when the expression levels of the Atg8 gene and Pink1 gene were increased, the cells could maintain youth. In addition, studies showed that the SIRT1 gene could initiate the generation and synthesis of mitochondria, and enable the cells to maintain health. It was discovered that animal experiments prove that the Ubl-5 gene could recover mitochondria activities, allowing old mice to rejuvenate.

Referring to FIG. 1, cDNA in Experiment group A to Experiment group F and Control group was respectively subjected to intracellular Atg8 gene expression analysis by Atg8-F (SEQ ID NO: 15) and Atg8-R (SEQ ID NO: 16), intracellular CCT2 gene expression analysis by CCT2-F (SEQ ID NO: 17) and CCT2-R (SEQ ID NO: 18), intracellular CCT5 gene expression analysis by CCT5-F (SEQ ID NO: 19) and CCT5-R (SEQ ID NO: 20), intracellular CCT6A gene expression analysis by CCT6A-F (SEQ ID NO: 21) and CCT6A-R (SEQ ID NO: 22), intracellular CCT7 gene expression analysis by CCT7-F (SEQ ID NO: 23) and CCT7-R (SEQ ID NO: 24), intracellular (CCT8 gene expression analysis by CCT8-F (SEQ ID NO: 25) and CCT8-R (SEQ ID NO: 26), intracellular Pink1 gene expression analysis by Pink1-F (SEQ ID NO: 27) and Pink1-R (SEQ ID NO: 28), intracellular STIR1 gene expression analysis by SIRT1-F (SEQ ID NO: 29) and SIRT1-R (SEQ ID NO: 30), and intracellular Ubl-5 gene expression analysis by Ubl-5-F (SEQ ID NO: 31) and Ubl-5-R (SEQ ID NO: 32). The results showed that the anti-aging genes in Experiment group E corresponding to SEQ ID NO: 5 and Experiment group F corresponding to SEQ ID NO: 6 were significantly upregulated as compared with those in Control group, and the fold of upregulation was shown in Table 5.

TABLE 5

| Anti-aging gene | SEQ ID NO: 5 (Experiment group E) | SEQ ID NO: 6 (Experiment group F) |
|---|---|---|
| Atg8 gene | 5.13 folds | 4.28 folds |
| CCT2 gene | 5.86 folds | 5.71 folds |
| CCT5 gene | 6.03 folds | 6.76 folds |
| CCT6A gene | 5.47 folds | 5.28 folds |
| CCT7 gene | 7.92 folds | 7.89 folds |
| CCT8 gene | 6.88 folds | 6.43 folds |
| Pink1 gene | 5.85 folds | 6.42 folds |
| SIRT1 gene | 6.62 folds | 6.52 folds |
| Ubl-5 gene | 5.24 folds | 5.16 folds |

As shown in Table 5, the gene expression level of the anti-aging gene in Experiment group E and Experiment group F was 4 to 8 folds of the gene expression level of the anti-aging gene in Control group. In addition, the increased gene expression level of the anti-aging gene suggested that the peptide has anti-aging capability. 2 types of amino acid sequences (SEQ ID NO: 5 to SEQ ID NO: 6) in Experiment group E and Experiment group F both have the capability of promoting expression of the anti-aging genes, so that a composition containing at least one amino acid sequence therein can also be used for promoting expression of the anti-aging genes. In addition, the composition can be used for minimizing skin pores, reducing wrinkles or achieving a combination of these effects.

Figure 3:
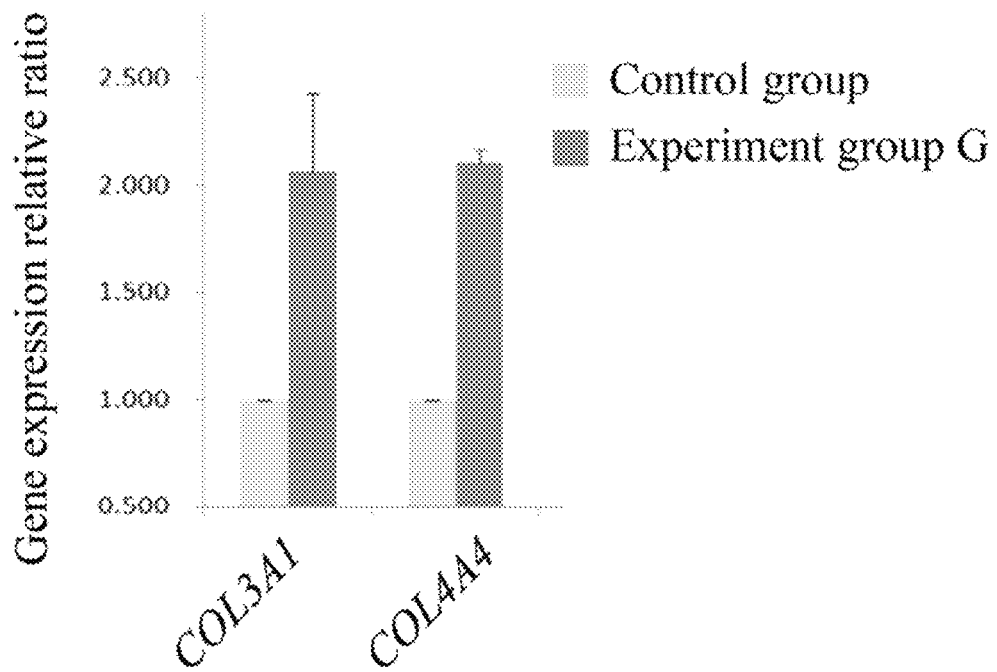
FIG. 3 is a bar chart showing relative ratios of COL3A1 and COL4A4 gene expression in Experiment group over Control group in accordance with some embodiments of the present invention.
Figure 4:
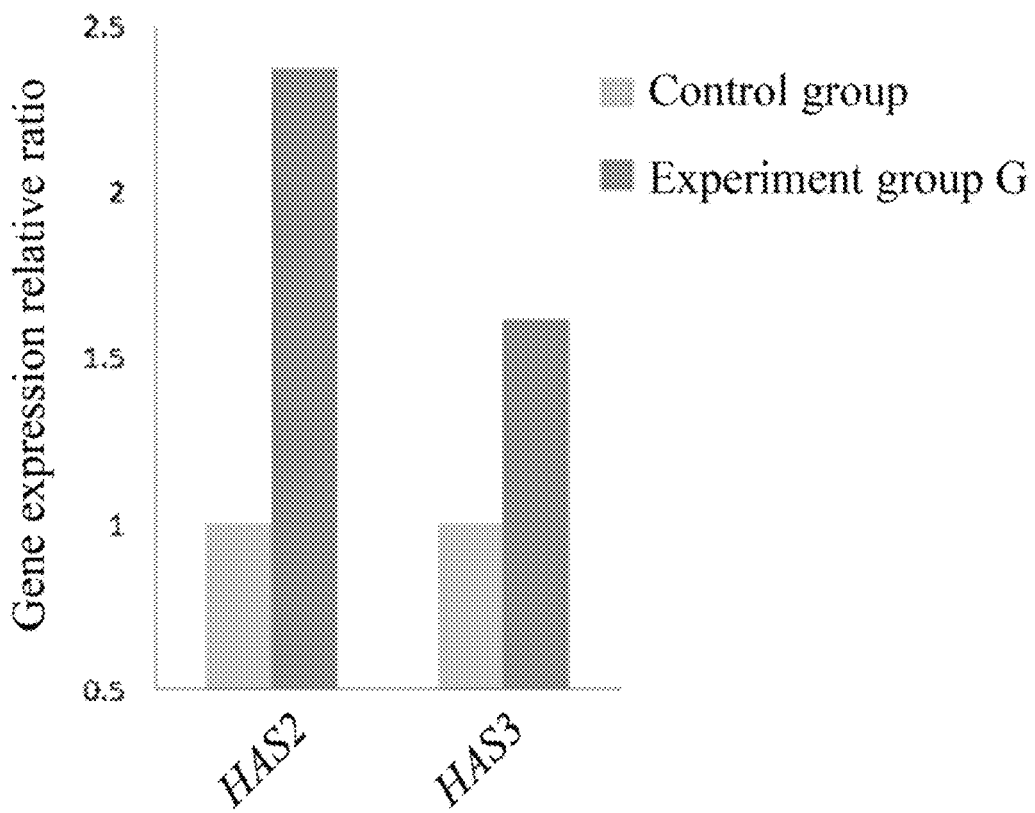
FIG. 4 is a bar chart showing relative ratios of HAS2 and HAS3 gene expression in Experiment group over Control group in accordance with some embodiments of the present invention.

(IV) Expression Analysis of Collagen Genes and Hyaluronan Synthase Genes in Composition Experiment Groups Then, the composition experiment groups (i.e., Experiment group G) and Control group were subjected to gene expression analysis of COL3A1 gene (Gene ID: 1281), (COL4A4 gene (Gene ID: 1286), HAS2 gene (Gene ID: 3037) and HAS3 gene (Gene ID: 3038), as shown in FIG. 3 and FIG. 4. It should be understood that the experiment groups as shown in FIG. 3 and FIG. 4 represent composition experiment groups (referred to as Experiment group G hereafter).

COL3A1 gene is a gene of type III collagen. COL4A4 gene is a gene of type IV collagen. Therefore, the increase in expression levels of the two genes suggests that the collagen content is increased. The HAS2 gene and the HAS3 gene are genes of hyaluronan synthase (HAS). Therefore, the increase in the HAS2 and HAS3 genes suggests that the HAS content is increased, the moisture holding ability of intercellular matrix of the skin is improved, the skin moisture is also increased, and the moisturizing effect is achieved.

Referring to FIG. 3, cDNA in Experiment group G and Control group was respectively subjected to intracellular type III collagen gene expression analysis by COL3A1-F (SEQ ID NO: 7) and COL3A1-R (SEQ ID NO: 8), and intracellular type IV collagen gene expression analysis by COL4A4-F (SEQ ID NO: 9) and COL4A4-R (SEQ ID NO: 10). The results showed that the ratio of Experiment group G to Control group was 2. In other words, the gene expression of type 111 collagen and type IV collagen in Experiment group G was twice of that in Control group.

Referring to FIG. 4, cDNA in Experiment group G and Control group was respectively subjected to HAS protein gene expression analysis by two groups of primers, HAS2-F (SEQ ID NO: 11) and HAS2-R (SEQ ID NO: 12), as well as HAS3-F (SEQ ID NO: 13) and HAS3-R (SEQ ID NO: 14). The results showed that the ratio of Experiment group G to Control group was about 1.5 to 2.5. In other words, the HAS protein gene expression in Experiment group G was at least 1.5 times higher than that in Control group.

Therefore, the anti-aging composition can promote the expression of the COL341 gene, the COL4A4 gene, the HAS2 gene and the HAS3 gene, and may be used for increasing collagen content, improving collagen density, improving skin moisture, minimizing skin pores, reducing wrinkles or achieving a combination of these effects.

Then, in order to confirm the effect of each of the amino acid sequences on mitochondria activities, human fibroblasts (CCD-966SK) and the individual peptides were co-cultured, and then, the mitochondrion activities was analyzed. 6 types of synthesized peptides were respectively subjected to mitochondria activity tests. In addition, the amino acid sequences of 6 types of synthesized peptides were respectively SEQ ID NO: 1, SEQ ID NO: 2, SEQ ID NO: 3, SEQ ID NO: 4, SEQ ID NO: 5 and SEQ ID NO: 6. The sequence numbers SEQ ID NO: 1 to SEQ ID NO: 6 will be referred to as groups.

(V) Mitochondria Activity Test

For mitochondria activity tests, after human fibroblasts and samples to be tested (such as peptides or compositions) were co-cultured, then, co-cultured cells were treated by a mitochondria membrane potential detection kit (containing a JC-1 mitochondria coloring agent, purchased from BD). Mitochondria activity test groups were divided into 7 groups. 6 Groups therein were peptide experiment groups, and 1 group was a control group, as shown in Table 6.

TABLE 6

| Mitochondria activity test groups | | Cell culture medium (2 ml) | Cells to be tested (1 × 10$^5$) | Samples to be tested |
|---|---|---|---|---|
| SEQ ID NO: 1 peptide experiment group | Experiment group H | X-VIVOTM 10 | Human fibroblasts | 15 μg of SEQ ID NO: 1 peptide was added |
| SEQ ID NO: 2 peptide experiment group | Experiment group I | X-VIVOTM 10 | Human fibroblasts | 10 μg of SEQ ID NO: 2 peptide was added |
| SEQ ID NO: 3 peptide experiment group | Experiment group J | X-VIVOTM 10 | Human fibroblasts | 10 μg of SEQ ID NO: 3 peptide was added |
| SEQ ID NO: 4 peptide experiment group | Experiment group K | X-VIVOTM 10 | Human fibroblasts | 10 μg of SEQ ID NO: 4 peptide was added |
| SEQ ID NO: 5 peptide experiment group | Experiment group L | X-VIVOTM 10 | Human fibroblasts | 10 μg of SEQ ID NO: 5 peptide |
| SEQ ID NO: 6 peptide experiment group | Experiment group M | X-VIVOTM 10 | Human fibroblasts | 25 μg of SEQ ID NO: 6 peptide was added |
| Control group | | X-VIVOTM 10 | Human fibroblasts | no peptide or composition was added |

It should be understood that Experiment group H to Experiment group M respectively correspond and equal to SEQ ID NO: 1, SEQ ID NO: 2, SEQ ID NO: 3, SEQ ID NO: 4, SEQ ID NO: 5 and SEQ ID NO: 6.

Firstly, each of the groups (Experiment group H to Experiment group M, and Control group) was co-cultured with 1×10$^5$ human fibroblasts in a cell culture plate containing 2 ml of cell culture medium (X-VIVO™ 10). Then, the samples to be tested for each of the group were added into corresponding culture plates according to Table 6, and were co-cultured with the human fibroblasts at 37° C. for 24 h. Control group was co-cultured for 24 h by a peptide-free culture medium under the same conditions.

Before the mitochondria activity test was performed, a JC-1 mitochondria coloring agent was prepared. Firstly, a 10× JC-1 buffer solution was preheated at 37° C., was then diluted into a 1× JC-1 buffer solution by a 1× phosphate buffer solution (PBS, purchased from Gibco), and was maintained at 37° C. after being uniformly mixed. 130 μl of dimethyl sulfoxide (DMSO) was added into a lyophilized JC-1 reagent to prepare a JC-1 stock solution. Then, the JC-1 stock solution was diluted 1000 folds by the 1× JC-1 buffer solution to prepare a JC-1 work solution.

After co-culture for 24 h, the cell culture medium in the culture plate was removed. The co-cultured cells were rinsed twice by PBS so as to remove the residual cell culture medium. The cells were trypsinized from the culture plate, and were collected into a 1.5 ml microcentrifuge tube to be centrifuged for 5 min at 400×g so as to form a primary supernatant and a primary cell precipitate. After the primary supernatant was removed, the primary cell precipitate was resuspended by PBS to form a primary cell solution. The primary cell solution was transferred into a 1.5 ml centrifuge tube to be centrifuged for 5 min at 400×g again so as to separate the primary cell solution into a secondary supernatant and a secondary cell precipitate. Then, after the secondary supernatant was removed, 100 μl of JC-1 work solution was added to the secondary cell precipitate and vortexed to form a secondary cell solution. The secondary cell solution was cultured in dark at a room temperature for 15 min.

Figure 2:
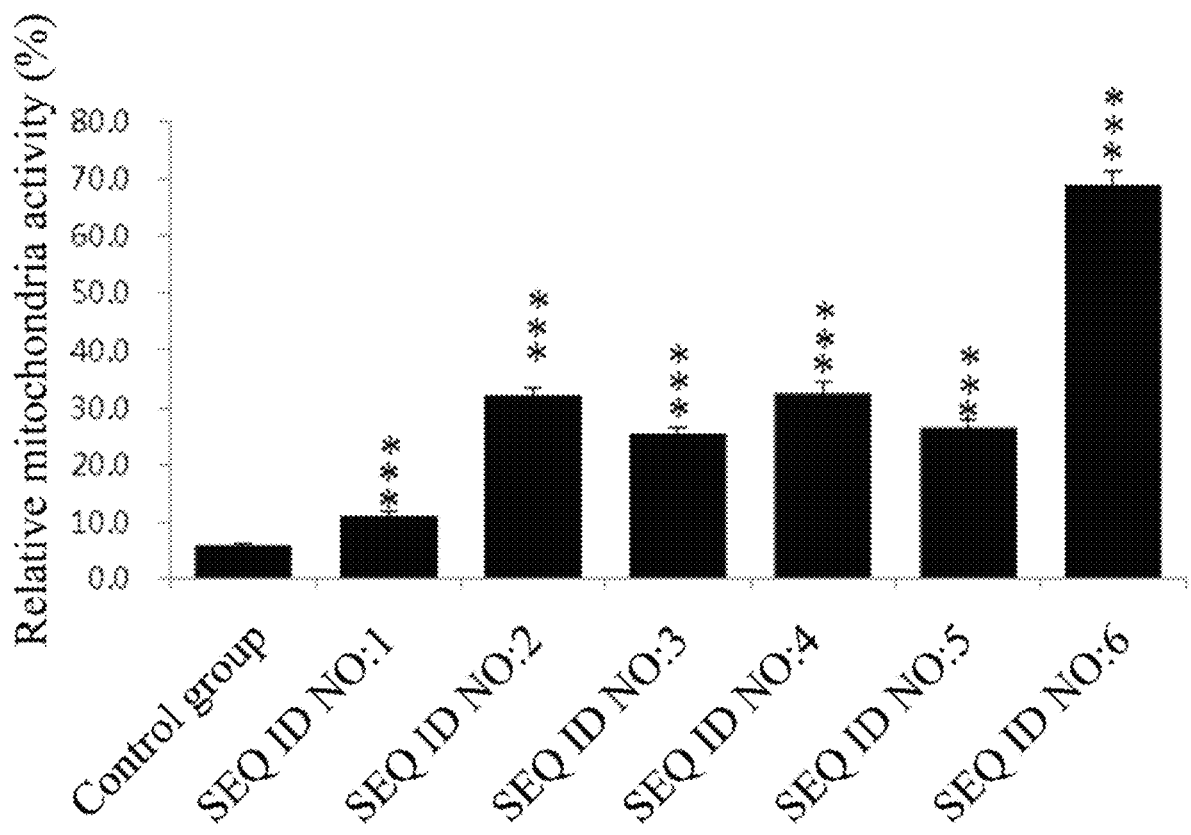
FIG. 2 is a bar chart showing relative mitochondria activities after treatment on human cells by a peptide in accordance with some embodiments of the present invention.

After cultured dark, the secondary cell solution was centrifuged for 5 min at 400×g. Then, redissolution by the 1× JC-1 buffer solution and 400×g centrifugation for 5 min were performed twice to form the samples to be tested for Experiment group H to Experiment group M. Finally, 6 groups of samples for Experiment group H to Experiment group M and samples for Control group were subjected to mitochondria activity test analysis by flow cytometry (purchased from Beckman). Experiment results are shown in FIG. 2. Standard deviations of the results were calculated by an STDEV formula of Excel software, and statistically significant differences were analyzed by one-tailed student t-test in the Excel software. In the drawings, "*" represents $p<0.05$, "" represents $p<0.01$, and "*" represents $p<0.0.001$. More "*" represents more significant statistical differences.

Referring to FIG. 2, the results showed that Experiment group I to Experiment group M corresponding to SEQ ID NO: 2, SEQ ID NO: 3, SEQ ID NO: 4, SEQ ID NO: 5 and SEQ ID NO: 6 all showed improved mitochondria activities. For example, as compared with Control group, SEQ ID NO: 2 improved 32.7% of the mitochondria activities, SEQ ID NO: 3 improved 25.6% of the mitochondria activities. SEQ ID NO: 4 improved 32.9% of the mitochondria activities. SEQ ID NO: 5 improved 26.7% of the mitochondria activities, and SEQ ID NO: 6 improved 68.9% of the mitochondria activities. When mitochondria activities are improved, the cells can maintain health. Therefore, all the peptides with the amino acid sequences of SEQ ID NO: 2, SEQ ID NO: 3, SEQ ID NO: 4, SEQ ID NO: 5 or SEQ ID NO: 6 can improve mitochondria activities. Therefore, when the composition is prepared from at least one or more of amino acid sequences of SEQ ID NO: 2 to SEQ ID NO: 6, mitochondria activities of the cells can also be improved.

Therefore, when the peptide is at least one amino acid sequence set forth in SEQ ID NO: 2 to SEQ ID NO: 6, the anti-aging composition containing the peptide can improve cell mitochondria activities. In addition, the composition can be used for improving skin conditions, such as minimizing skin pores, reducing wrinkles or achieving a combination of these effects.

In order to further confirm the effect of the composition on human skin, the composition was prepared from the peptides including the 6 types of amino acid sequences (i.e., SEQ ID NO: 1 to SEQ ID NO: 6). In addition, the composition used in experiments below was Basa fish skin peptide powder (purchased from Italgelatin, Italy) containing the 6 types of amino acid sequences (i.e., SEQ ID NO: 1 to SEQ ID NO: 6) as identified in Example I and Example II.

(VI) Experiment Group and Experiment Design

Subjects were asked to take the composition or commercially available fish collagen every day. After 4 weeks of observation, the skin conditions (wrinkles, skin moisture content and collagen density) of the subjects were observed by instruments (VISIA Complexion Analysis (Canfield Scientific, Inc., USA) and DermaLab® Combo collagen probe instrument), and the effect of the composition or the commercially available fish collagen on the skin was observed.

Among 13 subjects, the Experiment group (7 persons) was asked to take the composition and Control group (6 persons) was asked to take the commercially available fish collagen. In addition, the subjects needed to take 3 g of composition or commercially available fish collagen every day for 4 consecutive weeks. In addition, it should be noted that the "commercially available fish collagen" was not prepared from Basa skin.

(VII) In Vivo Effects

Test results were obtained by comparing values at the $0^{th}$ week and $4^{th}$ week altogether. The values at the $0^{th}$ week were measured before the test, and represented the skin conditions of all subjects before consuming the composition or the commercially available fish collagen. The values at the $4^{th}$ week were measured after consumption for four consecutive weeks. It should be noted that the skin conditions depicted in the drawings were shown by relative percentages. Standard deviations were calculated by an STDEV formula of Excel software, and statistically significant differences were analyzed by one-tailed student t-test in the Excel software. In the drawings, "*" represents $p<0.05$, "" represents $p<0.01$, and "*" represents $p<0.001$. When $p<0.05$, it represents that there are statistical differences.

Figure 5:
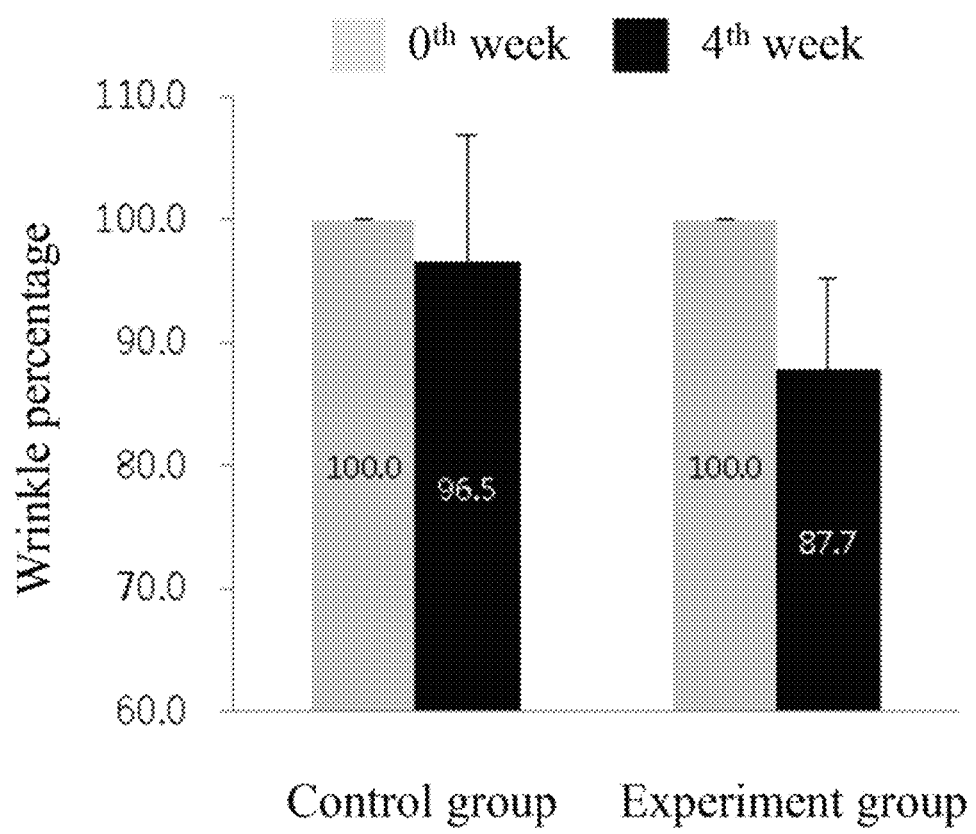
FIG. 5 is a bar chart showing wrinkle percentages of Experiment group and Control group at the $0^{th}$ week and $4^{th}$ week in accordance with some embodiments of the present invention.

Referring to FIG. 5, the results showed that the wrinkles in Control group were not reduced after consumption of the commercially available fish collagen for 4 consecutive weeks. The wrinkles in Experiment group were significantly reduced by 12.3% after continuous consumption of the composition. Therefore, as compared with Control group, Experiment group demonstrated that wrinkles could be effectively reduced by taking the anti-aging composition.

Figure 6:
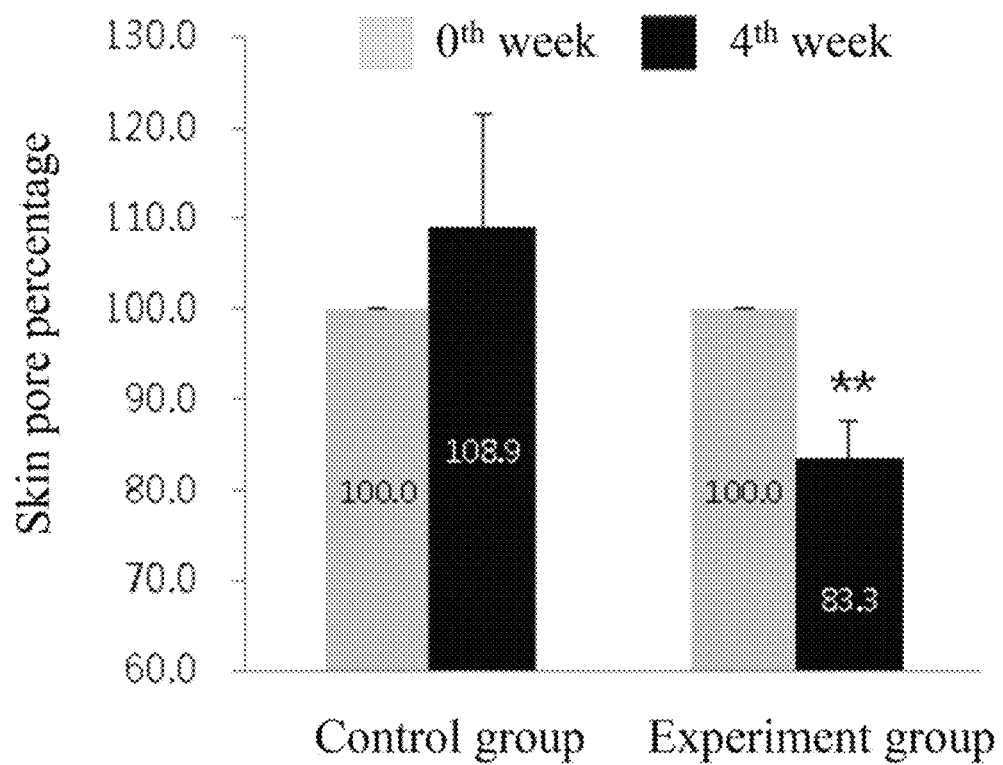
FIG. 6 is a bar chart showing skin pore percentages of Experiment group and Control group at the $0^{th}$ week and $4^{th}$ week in accordance with some embodiments of the present invention.
Figure 7:
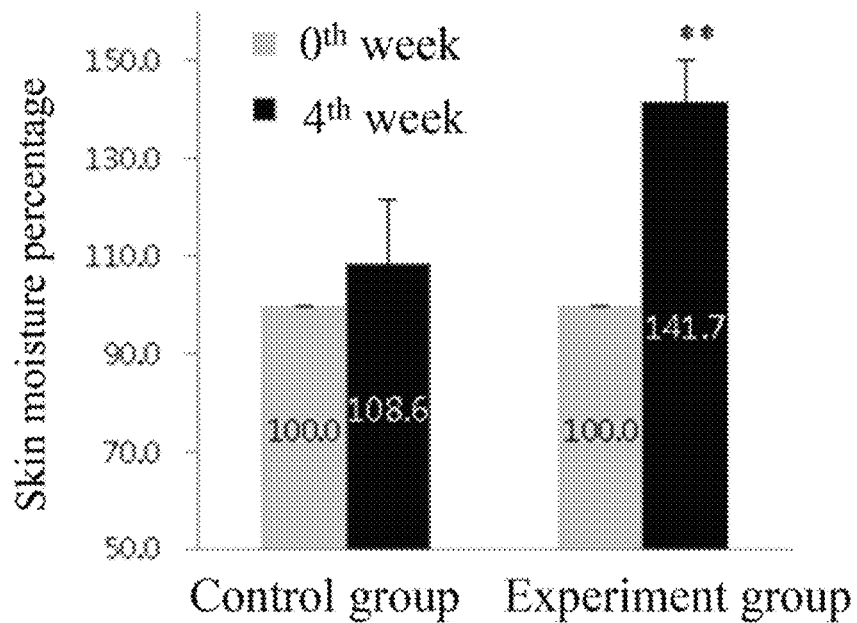
FIG. 7 is a bar chart showing skin moisture percentages of Experiment group and Control group at the $0^{th}$ week and $4^{th}$ week in accordance with some embodiments of the present invention.
Figure 8:
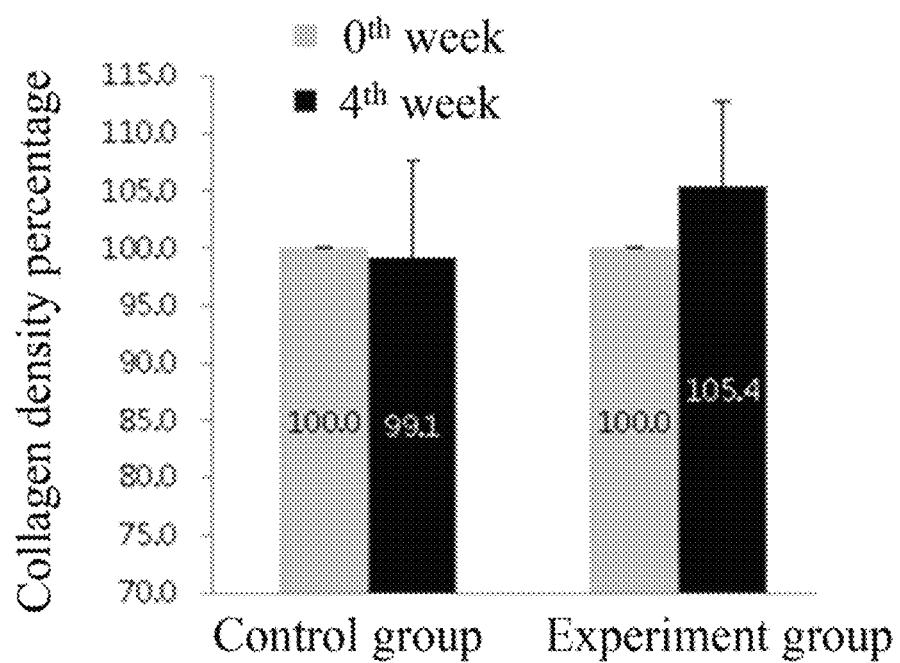
FIG. 8 is a bar chart showing collagen density percentages of Experiment group and Control group at the $0^{th}$ week and $4^{th}$ week in accordance with some embodiments of the present invention.

In addition, the values of Experiment group and Control group, such as skin pore percentage (as shown in FIG. 6), skin moisture percentage (as shown in FIG. 7) and skin collagen density (as shown in FIG. 8) were also compared.

Referring to FIG. 6, by comparing the skin pore percentages of Experiment group at the $0^{th}$ week and the $4^{th}$ week, the value of Experiment group was shown to decrease from 100% to 83.3%, which represented that the skin pores of the 7 subjects were reduced by 16.7%. On the other hand, when comparing the skin pore percentages of Control group at the $0^{th}$ week and the $4^{th}$ week, it was observed that the value was increased from 100% to 108.9%, which represented that the skin pore percentages of the 6 subjects were increased. Therefore, the skin pores could be effectively minimizing (for example, the size of skin pores could be decreased) by taking the composition.

Referring to FIG. 7, by comparing the skin moisture percentages of Experiment group at the $0^{th}$ week and the $4^{th}$ week, it can be observed that the value was improved from 100% to 141.7%, which represented that skin moisture of the 7 subjects was improved by 41.7%. On the other hand, when the skin moisture percentages of Control group at the $0^{th}$ week and the $4^{th}$ week were compared, it was observed that the value changed from 100% to 108.6%, which represented that loss of skin moisture of the 6 subjects were not significantly improved.

Referring to FIG. 8, by comparing the breast collagen density percentages of Experiment group at the $0^{th}$ week and the $4^{th}$ week, it can be observed that the value of Experiment group at the $4^{th}$ week was improved by 5.4% as compared with that at the $0^{th}$ week, which represented that the breast collagen density percentages of the 7 subjects were improved. When comparing the breast collagen density percentages of Control group at the $0^{th}$ week and the $4^{th}$ week, it was observed that the value at the $4^{th}$ week was reduced by 0.9% as compared with that at the 0 week. In other words, the effect of the composition for improving skin collagen density was more significant than that of the commercially available fish collagen. Therefore, as compared with Control group, the collagen density percentage could be effectively improved by taking the composition as in Experiment group.

Therefore, the anti-aging composition was prepared from the peptides including a plurality of peptides with at least one amino acid sequence as set forth in SEQ ID NO: 1 to SEQ ID NO: 6. The composition can be used for promoting anti-aging gene expression or/and improving mitochondria activities. In addition, the composition containing the peptide including 6 types of peptides (the amino acid sequences are respectively SEQ ID NO: 1 to SEQ ID NO: 6) possess the capability of promoting the expression of at least one gene of an Atg8 gene, a CCT2 gene, a CCT5 gene, a CCT6A gene, a CCT7 gene, a CCT8 gene, a Pink1 gene, an STIR1 gene, a Ubl-5 gene, a COL3A1 gene, a COL4A4 gene, an HAS2 gene and an HAS3 gene. In addition, the composition containing the peptide having at least one amino acid sequence as set forth in SEQ ID NO: 1 to SEQ ID NO: 6 could have at least one of the following effects: increasing collagen content, improving skin collagen density, improving skin moisture, minimizing skin pores and reducing wrinkles.

Based on the above, the peptide as the bioactive compound according to any embodiment of the present invention can be used for preparing the anti-aging composition. In addition, the peptide includes at least one amino acid sequence as set forth in SEQ ID NO: 1 to SEQ ID NO: 6. In some embodiments, the peptide as the bioactive compound can promote the expression of anti-aging genes and/or improve mitochondria activities. In some embodiments, the peptide as the bioactive compound can promote the expression of at least one gene of an Atg8 gene, a CCT2 gene, a CCT5 gene, a CCT6A gene, a CCT7 gene, a CCT8 gene, a Pink1 gene, an STIR1 gene and a Ubl-5 gene, and/or improve mitochondria activities. In addition, the composition can also be used for promoting the expression of at least one gene of a COL3A1 gene, a COL4A4 gene, an HAS2 gene and an HAS3 gene. In addition, the composition possesses anti-aging and cellular health maintaining capabilities. In addition, the composition can also be used for increasing collagen content, improving skin collagen density, improving skin moisture, minimizing skin pores, reducing wrinkles or achieving a combination of these effects.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for improving skin condition of a human in need thereof comprising administering to the human a composition comprising bioactive peptides from skin cells of *Pangasius bocourti*, wherein the peptides comprise at least one full-length sequence selected from the group consisting of SEQ ID NO: 3 and SEQ ID NO: 4.

2. The method according to claim 1, wherein the improvements of skin condition are reducing wrinkles, minimizing skin pores, improving skin moisture, or a combination thereof.

* * * * *

SEQUENCE LISTING

```
<160> NUMBER OF SEQ ID NOS: 32

<210> SEQ ID NO 1
<211> LENGTH: 8
<212> TYPE: PRT
<213> ORGANISM: Pangasius bocourti

<400> SEQUENCE: 1

Lys Gly Trp Pro Gly Thr Pro Gly
1               5

<210> SEQ ID NO 2
<211> LENGTH: 11
<212> TYPE: PRT
<213> ORGANISM: Pangasius bocourti

<400> SEQUENCE: 2

Pro Gly Ala Pro Gly Ser Ser Gly Pro Lys Gly
1               5                   10

<210> SEQ ID NO 3
<211> LENGTH: 12
<212> TYPE: PRT
<213> ORGANISM: Pangasius bocourti

<400> SEQUENCE: 3

Val Ala Glu Gly Ala Gln Gly Asn Ile Gly Pro Ala
1               5                   10

<210> SEQ ID NO 4
<211> LENGTH: 13
<212> TYPE: PRT
<213> ORGANISM: Pangasius bocourti

<400> SEQUENCE: 4

Asn Pro Gly Pro His Gly Gln Pro Gly Pro Pro Gly Pro
1               5                   10
```

<210> SEQ ID NO 5
<211> LENGTH: 9
<212> TYPE: PRT
<213> ORGANISM: Pangasius bocourti

<400> SEQUENCE: 5

Asp Lys Pro Leu Ile Pro Glu Gly Pro
1               5

<210> SEQ ID NO 6
<211> LENGTH: 12
<212> TYPE: PRT
<213> ORGANISM: Pangasius bocourti

<400> SEQUENCE: 6

Gly Pro Leu Gly Pro Ile Gly Pro Pro Gly Leu Pro
1               5                   10

<210> SEQ ID NO 7
<211> LENGTH: 21
<212> TYPE: DNA
<213> ORGANISM: Artificial Sequence
<220> FEATURE:
<223> OTHER INFORMATION: COL3A1-F

<400> SEQUENCE: 7
tggttgcacg gtaggaaaca t                                            21

<210> SEQ ID NO 8
<211> LENGTH: 20
<212> TYPE: DNA
<213> ORGANISM: Artificial Sequence
<220> FEATURE:
<223> OTHER INFORMATION: COL3A1-R

<400> SEQUENCE: 8
acagccttgc gtgttcgata                                              20

<210> SEQ ID NO 9
<211> LENGTH: 20
<212> TYPE: DNA
<213> ORGANISM: Artificial Sequence
<220> FEATURE:
<223> OTHER INFORMATION: COL4A4-F

<400> SEQUENCE: 9
ctgggtgctg tgtgttttga                                              20

<210> SEQ ID NO 10
<211> LENGTH: 20
<212> TYPE: DNA
<213> ORGANISM: Artificial Sequence
<220> FEATURE:
<223> OTHER INFORMATION: COL4A4-R

<400> SEQUENCE: 10
tgagtcttgt tttgccctgc                                              20

<210> SEQ ID NO 11
<211> LENGTH: 20
<212> TYPE: DNA
<213> ORGANISM: Artificial Sequence
<220> FEATURE:
<223> OTHER INFORMATION: HAS2-F

<400> SEQUENCE: 11
cggtgctcca aaaaggcaaa                                           20

<210> SEQ ID NO 12
<211> LENGTH: 20
<212> TYPE: DNA
<213> ORGANISM: Artificial Sequence
<220> FEATURE:
<223> OTHER INFORMATION: HAS2-R

<400> SEQUENCE: 12
acacaatgag ttgggcgaga                                           20

<210> SEQ ID NO 13
<211> LENGTH: 20
<212> TYPE: DNA
<213> ORGANISM: Artificial Sequence
<220> FEATURE:
<223> OTHER INFORMATION: HAS3-F

<400> SEQUENCE: 13
cacccatggg ggcttaactt                                           20

<210> SEQ ID NO 14
<211> LENGTH: 20
<212> TYPE: DNA
<213> ORGANISM: Artificial Sequence
<220> FEATURE:
<223> OTHER INFORMATION: HAS3-R

<400> SEQUENCE: 14
ctgcaggtcc cagttcacat                                           20

<210> SEQ ID NO 15
<211> LENGTH: 20
<212> TYPE: DNA
<213> ORGANISM: Artificial Sequence
<220> FEATURE:
<223> OTHER INFORMATION: Atg8-F

<400> SEQUENCE: 15
ccgcagtagg tggcaaagta                                           20

<210> SEQ ID NO 16
<211> LENGTH: 20
<212> TYPE: DNA
<213> ORGANISM: Artificial Sequence
<220> FEATURE:
<223> OTHER INFORMATION: Atg8-R

<400> SEQUENCE: 16
ggagtcggag aggattgctg                                           20

<210> SEQ ID NO 17
<211> LENGTH: 18
<212> TYPE: DNA
<213> ORGANISM: Artificial Sequence
<220> FEATURE:
<223> OTHER INFORMATION: CCT2-F

<400> SEQUENCE: 17
cactggtgcg attatttg                                             18

<210> SEQ ID NO 18
<211> LENGTH: 18
<212> TYPE: DNA

```
<213> ORGANISM: Artificial Sequence
<220> FEATURE:
<223> OTHER INFORMATION: CCT2-R

<400> SEQUENCE: 18
cccagcaaat atcagaag                                                  18

<210> SEQ ID NO 19
<211> LENGTH: 19
<212> TYPE: DNA
<213> ORGANISM: Artificial Sequence
<220> FEATURE:
<223> OTHER INFORMATION: CCT5-F

<400> SEQUENCE: 19
ataaatgtga ggctgaatc                                                 19

<210> SEQ ID NO 20
<211> LENGTH: 18
<212> TYPE: DNA
<213> ORGANISM: Artificial Sequence
<220> FEATURE:
<223> OTHER INFORMATION: CCT5-R

<400> SEQUENCE: 20
acttgtcact tgtggcac                                                  18

<210> SEQ ID NO 21
<211> LENGTH: 21
<212> TYPE: DNA
<213> ORGANISM: Artificial Sequence
<220> FEATURE:
<223> OTHER INFORMATION: CCT6A-F

<400> SEQUENCE: 21
tgtgtatctt aatccagact c                                              21

<210> SEQ ID NO 22
<211> LENGTH: 20
<212> TYPE: DNA
<213> ORGANISM: Artificial Sequence
<220> FEATURE:
<223> OTHER INFORMATION: CCT6A-R

<400> SEQUENCE: 22
cgtttcacct aagagttgtc                                                20

<210> SEQ ID NO 23
<211> LENGTH: 19
<212> TYPE: DNA
<213> ORGANISM: Artificial Sequence
<220> FEATURE:
<223> OTHER INFORMATION: CCT7-F

<400> SEQUENCE: 23
gattggccat ttaagaaac                                                 19

<210> SEQ ID NO 24
<211> LENGTH: 18
<212> TYPE: DNA
<213> ORGANISM: Artificial Sequence
<220> FEATURE:
<223> OTHER INFORMATION: CCT7-R

<400> SEQUENCE: 24
ccatacccaa acctaagc                                                  18
```

<210> SEQ ID NO 25
<211> LENGTH: 17
<212> TYPE: DNA
<213> ORGANISM: Artificial Sequence
<220> FEATURE:
<223> OTHER INFORMATION: CCT8-F

<400> SEQUENCE: 25
acccggaggt ggagcaa                                                17

<210> SEQ ID NO 26
<211> LENGTH: 25
<212> TYPE: DNA
<213> ORGANISM: Artificial Sequence
<220> FEATURE:
<223> OTHER INFORMATION: CCT8-R

<400> SEQUENCE: 26
ggacatgtct ctccatatga tgtga                                       25

<210> SEQ ID NO 27
<211> LENGTH: 20
<212> TYPE: DNA
<213> ORGANISM: Artificial Sequence
<220> FEATURE:
<223> OTHER INFORMATION: Pink1-F

<400> SEQUENCE: 27
gtggaacatc tcggcaggtt                                             20

<210> SEQ ID NO 28
<211> LENGTH: 26
<212> TYPE: DNA
<213> ORGANISM: Artificial Sequence
<220> FEATURE:
<223> OTHER INFORMATION: Pink1-R

<400> SEQUENCE: 28
cctctcttgg attttctgta agtgac                                      26

<210> SEQ ID NO 29
<211> LENGTH: 21
<212> TYPE: DNA
<213> ORGANISM: Artificial Sequence
<220> FEATURE:
<223> OTHER INFORMATION: SIRT1-F

<400> SEQUENCE: 29
tgctggccta atagagtggc a                                           21

<210> SEQ ID NO 30
<211> LENGTH: 20
<212> TYPE: DNA
<213> ORGANISM: Artificial Sequence
<220> FEATURE:
<223> OTHER INFORMATION: SIRT1-R

<400> SEQUENCE: 30
ctcagcgcca tggaaaatgt                                             20

<210> SEQ ID NO 31
<211> LENGTH: 20
<212> TYPE: DNA
<213> ORGANISM: Artificial Sequence
<220> FEATURE:

```
<223> OTHER INFORMATION: Ub1-5-F

<400> SEQUENCE: 31
cctcttcctc gttctaccgc                                              20

<210> SEQ ID NO 32
<211> LENGTH: 20
<212> TYPE: DNA
<213> ORGANISM: Artificial Sequence
<220> FEATURE:
<223> OTHER INFORMATION: Ub1-5-R

<400> SEQUENCE: 32
ctagctggag ctcgaatcgc                                              20
```